US007925445B2

(12) United States Patent
Petrilla et al.

(10) Patent No.: US 7,925,445 B2

(45) Date of Patent: Apr. 12, 2011

(54) READ-WRITE ASSAY SYSTEM

(75) Inventors: John Francis Petrilla, Palo Alto, CA (US); Patrick T. Petruno, San Jose, CA (US); Daniel B. Roitman, Menlo Park, CA (US); Rong Zhou, Sunnyvale, CA (US); Michael John Brosnan, Fremont, CA (US)

(73) Assignee: Alverix, Inc., San Jose, CA (US)

( * ) Notice: Subject to any disclaimer, the term of this patent is extended or adjusted under 35 U.S.C. 154(b) by 110 days.

(21) Appl. No.: 11/004,390

(22) Filed: Dec. 3, 2004

(65) Prior Publication Data

US 2006/0122782 A1 Jun. 8, 2006

(51) Int. Cl.

| | |
|---|---|
| ***G01N 33/48*** | (2006.01) |
| ***G01N 33/543*** | (2006.01) |
| ***C12Q 1/00*** | (2006.01) |
| ***A61B 5/00*** | (2006.01) |

(52) U.S. Cl. ................ 702/19; 702/20; 435/4; 600/300; 436/518

(58) Field of Classification Search ........................ None
See application file for complete search history.

(56) References Cited

U.S. PATENT DOCUMENTS

| | | | |
|---|---|---|---|
| 4,632,901 A | 12/1986 | Valkirs et al. | |
| 5,445,970 A | 8/1995 | Rohr | |
| 5,591,645 A | 1/1997 | Rosenstein | |
| 5,602,040 A | 2/1997 | May et al. | |
| 5,622,871 A | 4/1997 | May et al. | |
| 5,714,389 A | 2/1998 | Charlton et al. | |
| 5,798,273 A | 8/1998 | Shuler et al. | |
| 5,879,951 A | 3/1999 | Sy | |
| 5,925,573 A | 7/1999 | Colin et al. | |
| 5,958,790 A | 9/1999 | Cerny | |
| 5,981,297 A | 11/1999 | Baselt | |
| 6,394,952 B1 * | 5/2002 | Anderson et al. | 600/300 |
| 6,727,103 B1 | 4/2004 | Reber et al. | |
| 2004/0214347 A1 | 10/2004 | LaBorde et al. | |
| 2004/0241752 A1 | 12/2004 | Anderson et al. | |

FOREIGN PATENT DOCUMENTS

| | | |
|---|---|---|
| EP | 1 048 723 B1 | 4/2004 |
| EP | 1 396 725 A1 | 10/2004 |

OTHER PUBLICATIONS

Database WPI Section E1, Week 200422, Derwent Publications Ltd., London, GB: AN 2004-228008 XP002391549 & CN 1 464 422 A, Dec. 31, 2003, Abstract.

* cited by examiner

*Primary Examiner* — Shubo (Joe) Zhou

(74) *Attorney, Agent, or Firm* — K&L Gates LLP

(57) ABSTRACT

A read-write assay system includes providing an assay device; and writing assay device information to the assay device for subsequent reading of the assay device information from the assay device; or performing an assay with the assay device and subsequent writing of the assay related information to the assay device or reading of assay related information from the assay device.

12 Claims, 1 Drawing Sheet

READ-WRITE ASSAY SYSTEM

BACKGROUND ART

The present invention relates generally to medical testing, and more particularly to lateral flow assay.

In patient care, immunoassay technology provides simple and relatively quick means for determining the presence of analytes in a subject sample. Analytes are substances of interest or clinical significance that may be present in biological or non-biological fluids. The analytes can include antibodies, antigens, drugs, or hormones.

The analyte of interest is generally detected by reaction with a capture agent, which yields a resultant or complex that is more easily detected and measured than the original analyte. Detection methods can include a change in absorbance, particularly a change in color, change in fluorescence, change in luminescence, change in electrical potential at a surface, change in other optical properties, or any other easily measured physical property indicating the presence or absence of an analyte in a sample.

New immunoassay devices have been developed that play an important role in areas such as clinical chemistry. They are used by skilled clinicians and laypersons alike. Thus, there is a strong impetus to provide devices that are simple and reliable. Desirably, the assays are single-step tests wherein the user need only apply the sample prior to viewing the result. Single-step tests obviate the necessity of performing complicated and time consuming processing steps that may introduce errors in the end result.

Immunoassay tests are often critical to patient care. Assays are routinely performed to detect the presence of particular analytes that are present when a human or non-human subject has a particular disease or condition, such as HIV, flu, alcohol, drugs, ovulation, pregnancy, etc.

Immunoassay technology now allows for assay tests to be performed without the complex and expensive equipment used in hospitals and laboratory settings. Kits for performing assays are now available for home or point of care use to quickly determine the presence of a disease or condition by providing qualitative results for the analyte or tested condition. These kits generally include strips that provide a visual indication when the analyte being sought is detected.

Generally, these assays have an extended base layer on which a differentiation can be made between a sample application region and an evaluation region. In typical use, the sample is applied to the sample application region, flows along a liquid transport path, which runs parallel to the base layer, and then flows into the evaluation region. A capture reagent is present in the evaluation region, and the captured analyte can be detected by a variety of protocols to detect visible moieties as described above associated with the captured analyte.

The above assays are called lateral flow assays or immunoassays and are currently single use and disposable.

DISCLOSURE OF THE INVENTION

The present invention provides a read-write assay system including providing an assay device; and writing assay device information to the assay device for subsequent reading of the assay device information from the assay device; or performing an assay with the assay device and subsequent writing of the assay related information to the assay device or reading of assay related information from the assay device.

Certain embodiments of the invention have other advantages in addition to or in place of those mentioned above. The advantages will become apparent to those skilled in the art from a reading of the following detailed description when taken with reference to the accompanying drawings.

BEST MODE FOR CARRYING OUT THE INVENTION

Figure 1:
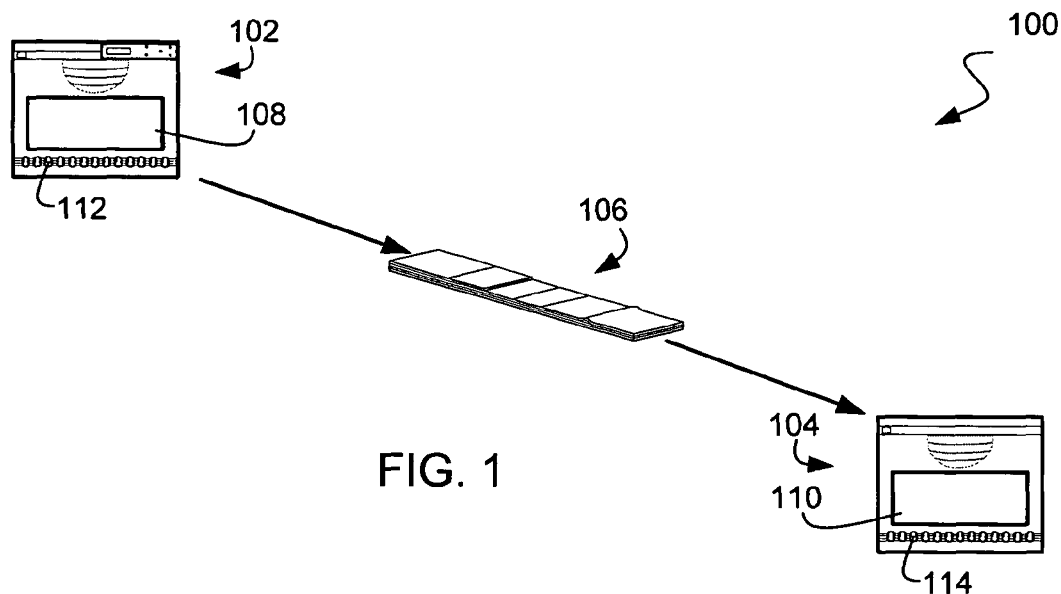
FIG. 1 is a read-write assay system according to one embodiment of the present invention.

In the following description, numerous specific details are given to provide a thorough understanding of the invention. However, it will be apparent to one skilled in the art that the invention may be practiced without these specific details. In order to avoid obscuring the present invention, some well-known devices are not disclosed in detail.

Likewise, the drawings showing embodiments of the apparatus are semi-diagrammatic and not to scale and, particularly, some of the dimensions are for the clarity of presentation and are shown greatly exaggerated in the FIGs. Where multiple embodiments are disclosed and described having some features in common, for clarity and ease of illustration and description thereof like features one to another will ordinarily be described with like reference numerals.

Referring now to FIG. 1, therein is shown a read-write assay system 100 according to one embodiment of the present invention. The read-write assay system 100 has a simple read-write device 102 intended to be used in a manufacturing location, a read-write device 104 intended to be used in a home or at a point of care location, and a lateral flow assay device 106.

The terms reading and writing are used in the present invention to define writing and reading using a powered write or read device, as contrasted to a writing by printing or handwriting and reading by eye of a printed or handwritten label.

The manufacturing location includes the location at which the lateral flow assay device 106 is manufactured, calibrated, packaged, or otherwise processed for an end user. It may even be a physician's office.

The point of care location includes a physician's office as well as other sites where the lateral flow assay device 106 can be used.

The read-write devices 102 and 104 are electro-magnetic, electronic, optical, or other types of read and write devices to read and write information and data on appropriate media either with or without contact. The read-write devices 102 and 104 are able to read back what has just written and, at a later time read it again without performing an assay or over writing the written information. The initial assay results may be write-protected to prevent over writing for legal reasons. These types of devices can be inexpensive and portable so as to be readily affordable for home use, a physician's office, or at the point of care.

The read-write devices 102 and 104 can have simple liquid crystal displays 108 and 110, respectively, for review of the data and simple keypads 112 and 114, respectively, for entry of data. These devices can also be operated individually for single lateral flow assay device 106 or automatically for a number of lateral flow assay devices.

Figure 2:
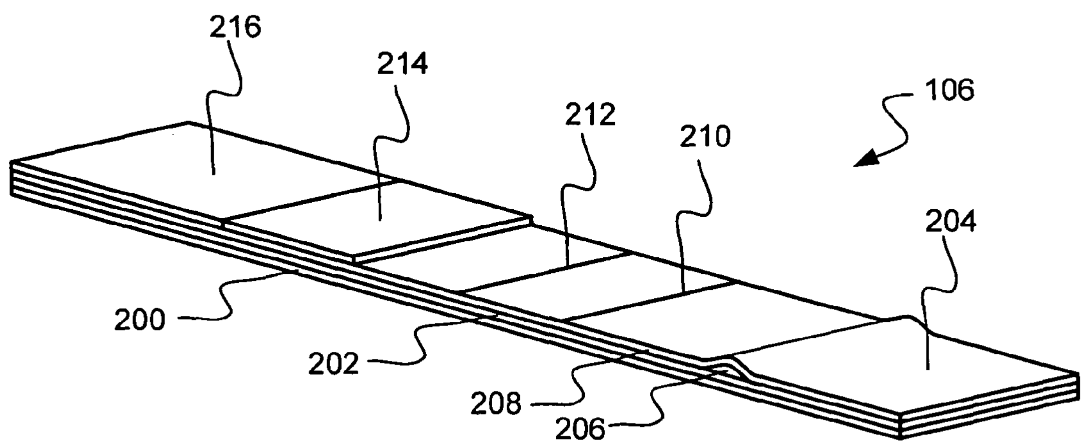
FIG. 2 is a lateral flow assay device in one embodiment of the present invention.

Referring now to FIG. 2, therein is shown the lateral flow assay device 106 in one embodiment of the present invention.

The lateral flow assay device 106 has a multi-layer configuration with a rectangular backing 200 topped by an adhesive 202. For ease of manufacture, the adhesive 202 can be a pressure sensitive adhesive.

A sample pad 204 is bonded to the rectangular backing 200 by the pressure sensitive adhesive at one end of the configuration. The sample analyte in a fluid is deposited on the sample pad 204 for assaying.

A conjugate pad 206 is located adjacent the sample pad 204. The conjugate pad 206 contains the labeling substance for the analyte to be assayed, forming a conjugate. This conjugate is then mixed with the sample analyte and, if the analyte to be assayed is present in the fluid, the labeling substance will give an indication that the analyte to be assayed is present.

A wicking layer 208 of a material such as nitrocellulose is on top of the conjugate pad 206 to promote capillary action and movement of the sample analyte in fluid down the wicking layer 208. The wicking layer 208 preferably has at least two spaced apart lines: a capture line 210 and control line 212. They are preferably at right angles to the lengthwise axis of the rectangular backing 200. The capture line 210 and control line 212 preferably permeate the wicking layer 208 and have easily read widths.

An absorbent pad 214 is bonded over an end of the wicking layer 208. The absorbent pad 214 draws the mixed conjugate from the conjugate pad 206 along the wicking layer 208.

A read-write pad 216 is bonded over an end of the absorbent pad 214 and the end of the rectangular backing 200 opposite the sample pad 204. The read-write pad 216 is a recording media upon which data can be read and written electro-magnetically, electronically, optically, etc.

The read-write pad 216 allows the read-write device 102 of FIG. 1 at the manufacturer's plant to be used to write lateral flow assay device information. The lateral flow assay device information can include, but is not limited to, manufacturer identity, lot code, device code, calibration information, configuration information, etc.

At the time of the assay, specific device information can link the lateral flow assay device 106 with the assay to be performed. The specific lateral flow assay device information can include, but is not limited to, the type of assay the lateral flow assay device 106 actually performs, its shelf life, the correct test conditions (such as time and temperature), etc.

The read-write pad 216 allows the read-write device 104 of FIG. 1 at the point of use to read data to protect against misdiagnosis by using the wrong lateral flow assay device 106.

Also, the read-write device 104 could also contain a lateral flow assay device reader to take the actual assay readings. Thus, by providing calibration and/or configuration information, it is possible to improve the accuracy of the results by calibrating and/or configuring the lateral flow assay device reader.

Calibration can provide valid and meaningful results for semi-quantitative and quantitative detections. Calibration methods are often critical to provide accurate, reliable and reproducible results, especially when the environments and conditions under which the measurements are commenced are not carefully controlled.

Two calibration methods, external and internal calibrations, are commonly employed.

In the external calibration method, a standard curve is usually obtained from standard samples containing a series of a known amount of analyte, and the results obtained from the samples are then compared with the standard curve to extract the information regarding the presence and/or amount of the analyte in the sample.

External calibration methods are often subject to interference from environmental and batch-to-batch variations, and sometimes are not reliable. When an instrument or measuring device is used, it is also subject to interference from the instability of the instrument or device.

Configuration information is also valuable such as wavelengths used, intensity of calibration features, background noise, etc. under which the lateral flow assay device reader operates can be provided so it can be adapted to the specific test to provide more accurate and/or sensitive results.

After the assay, the read-write device 104 could use the read-write pad 216 to record lateral flow assay related information such as the patient name, chart number, test results, etc. Since the information will be on and associated with the lateral flow assay device 106, manual recording mistakes will be reduced and traceability will be improved. Further, time and date stamps, operator and test item identity can be written to additionally improve traceability, reduce the possibility of testing mistakes, identity mistakes, etc.

As a further benefit, the lateral flow assay device 106 provides a means to correlate test results among operators and/or lateral flow assay device readers.

Figure 3:
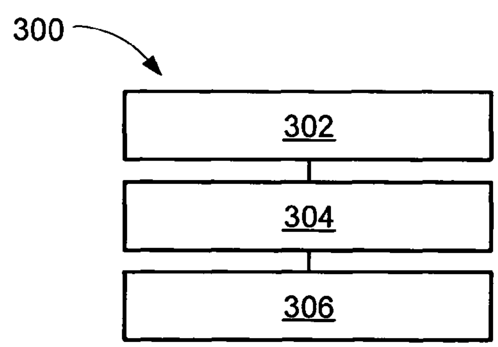
FIG. 3 is a read-write assay system for using an embodiment of the present invention.

Referring now to FIG. 3, therein is shown a read-write assay system 300 for using an embodiment of the present invention. The read-write assay system 300 includes providing an assay device in a block 302, and writing assay device information to the assay device for subsequent reading of the assay device information from the assay device in a block 304, or performing an assay with the assay device, and writing of the assay related information to the assay device or reading of assay related information from the assay device in a block 306.

As usage becomes more common and includes monitoring a condition with multiple assays over a period of time, it will become increasingly valuable to provide a means of traceability on the assay strip, e.g. time and date stamps." Another use that may be valuable is as evidence in legal proceedings, e.g. DUI cases.

Thus, it has been discovered that the read-write assay system of the present invention furnish important and previously unavailable solutions, capabilities, and functional advantages for lateral flow assay devices.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hither-to-fore set forth herein or shown in the accompanying drawings are to be interpreted in an illustrative and non-limiting sense.

The invention claimed is:

1. A method for using a read-write assay system comprising:

providing an assay device having a read-write pad adjoining and abutting an end surface of an absorbent pad and over a backing, the read-write pad arranged opposite a sample pad of the assay device and bonded over an end of the absorbent pad and an end of the backing; and writing assay device information to the read-write pad of the assay device for subsequent:

reading of the assay device information from the read-write pad of the assay device;

performing an assay with the assay device and subsequent:

writing of assay related information to the read-write pad of the assay device; or reading of assay related information from the read-write pad of the assay device.

2. The method as claimed in claim 1 wherein:

writing the assay device information occurs at a manufacturing location; and writing the assay related information occurs at a point of care location.

3. The method as claimed in claim 1 wherein writing the assay device information, reading the assay device information, or writing the assay related information is performed electro-magnetically.

4. A method for using a read-write assay system comprising:

providing a lateral flow assay device having recording media thereon, the recording media comprising a read-write pad adjoining and abutting an end surface of an absorbent pad and over a backing opposite a sample pad of the lateral flow assay device such that the read-write pad is arranged in end-to-end contact with the absorbent pad, the read-write pad bonded over an end of the absorbent pad and an end of the backing; and writing lateral flow assay device information to the recording media on the lateral flow assay device for subsequent:

reading of the lateral flow assay device information from the recording media on the lateral flow assay device;

performing a lateral flow assay with the lateral flow assay device to obtain lateral flow assay related information and subsequent:

writing of the lateral flow assay related information to the recording media on the lateral flow assay device, the lateral flow assay related information including one of an operator identifier and an assay device reader identifier; or reading of the lateral flow assay related information from the recording media on the lateral flow assay device.

5. The method as claimed in claim 4 wherein:

writing the lateral flow assay device information occurs at a manufacturing location; and writing the lateral flow assay related information occurs at a point of use location.

6. The method as claimed in claim 4 wherein writing the lateral flow assay device information, reading the lateral flow assay device information, or writing the lateral flow assay related information is performed electro-magnetically on the recording media.

7. A read-write assay system comprising:

an assay device for performing an assay; and a pad adjoining and abutting an end surface of an absorbent pad and over a backing, the pad arranged opposite a sample pad and in end-to-end contact with the absorbent pad of the assay device for writing assay device information to the assay device for subsequent:

reading of the assay device information from the pad on the assay device;

performing an assay with the assay device; and writing of assay related information to the pad on the assay device.

8. The system as claimed in claim 7 further comprising:

a read-write device for writing the assay device information at a manufacturing location; and a read-write device for writing the assay related information at a point of care location.

9. The system as claimed in claim 7 wherein the pad for writing the assay device information, reading the assay device information, or writing the assay related information uses electro-magnetic reading and writing.

10. A read-write assay system comprising:

a lateral flow assay device; and a recording media pad arranged in end-to-end contact with an absorbent pad of the lateral flow assay device for writing lateral flow assay device information to the recording media on the lateral flow assay device for subsequent:

reading lateral flow assay device information from the recording media pad on the lateral flow assay device;

performing a lateral flow assay with the lateral flow assay device to obtain lateral flow assay related information;

writing of the lateral flow assay related information including one of a test operator identifier and an assay device reader identifier to the recording media pad which is bonded to the absorbent pad of the lateral flow assay device; or reading of the lateral flow assay related information from the recording media pad bonded to the lateral flow assay device.

11. The system as claimed in claim 10 further comprising:

a read-write device for writing the lateral flow assay device information at a manufacturing location; or a read-write device for writing the lateral flow assay related information at a point of use location.

12. The system as claimed in claim 10 wherein the recording media pad for writing the lateral flow assay device information, reading the lateral flow assay device information, or writing the lateral flow assay related information is read from and written to electro-magnetically.

* * * * *